United States Patent
Johnson et al.

(10) Patent No.: US 6,596,011 B2
(45) Date of Patent: Jul. 22, 2003

(54) EMBOLI EXTRACTION CATHETER AND VASCULAR FILTER SYSTEM

(75) Inventors: Kirk Johnson, Weston, FL (US); Patrick O'Neill, Doylestown, PA (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/879,492

(22) Filed: Jun. 12, 2001

(65) Prior Publication Data

US 2002/0188313 A1 Dec. 12, 2002

(51) Int. Cl.[7] .............................................. A61M 29/00
(52) U.S. Cl. ....................................... 606/200; 606/159
(58) Field of Search ................................. 606/159, 190, 606/191, 194, 200

(56) References Cited

U.S. PATENT DOCUMENTS

| | | | |
|---|---|---|---|
| 3,952,747 A | 4/1976 | Kimmell, Jr. ............... 128/303 |
| 4,545,390 A | 10/1985 | Leary .......................... 128/772 |
| 4,619,274 A | 10/1986 | Morrison ..................... 128/772 |
| 4,688,553 A | 8/1987 | Metals ........................ 128/1 R |
| 4,727,873 A | 3/1988 | Mobin-Uddin .......... 128/303 R |
| 5,095,915 A | 3/1992 | Engelson ..................... 128/772 |
| 5,814,064 A | 9/1998 | Daniel et al. ................ 606/200 |
| 5,827,324 A | 10/1998 | Cassell et al. .............. 606/200 |
| 5,910,154 A | * 6/1999 | Tsugita et al. ............... 606/200 |
| 6,001,118 A | 12/1999 | Daniel et al. ................ 606/200 |
| 6,022,336 A | 2/2000 | Zadno-Azizi et al. |
| 6,053,932 A | 4/2000 | Daniel et al. ................ 606/200 |
| 6,135,991 A | 10/2000 | Muni et al. .................. 604/509 |
| 6,152,909 A | * 11/2000 | Bagaoisan et al. .......... 604/173 |
| 6,159,195 A | * 12/2000 | Ha et al. ................ 604/103.04 |
| 6,165,200 A | * 12/2000 | Tsugita et al. ............... 606/200 |
| 6,179,861 B1 | 1/2001 | Khosravi et al. ........... 606/200 |
| 6,203,561 B1 | 3/2001 | Ramee et al. |
| 6,371,971 B1 | * 4/2002 | Tsugita et al. ............... 606/200 |

* cited by examiner

*Primary Examiner*—Michael J. Milano
*Assistant Examiner*—Victor Nguyen
(74) *Attorney, Agent, or Firm*—Paul A. Coletti (57) ABSTRACT

An emboli extraction catheter and vascular filter system comprising a guidewire, a vascular filter attached near the distal end of the guidewire, and an emboli extraction catheter. The vascular filter has a smaller first diameter for insertion into the lumen of a vessel, and a second larger diameter for expanding to substantially equal the diameter of the lumen and to be placed in generally sealing relationship with the lumen. The emboli extraction catheter is a flexible catheter comprising a hub attached to the proximal end of the catheter. The hub further comprises a sideport and means for maintaining a seal on the guidewire. The emboli extraction catheter can be used to aspirate embolic particulates, so as to avoid their accidental release after they are captured in a vascular filter, and can also be used to empty full vascular filters of embolic particulates which may block distal flow.

12 Claims, 4 Drawing Sheets

EMBOLI EXTRACTION CATHETER AND VASCULAR FILTER SYSTEM

BACKGROUND

1. Field of the Invention

The present invention relates to the treatment of vascular disease, and more particularly to an emboli extraction catheter and vascular filter system for use during medical procedures.

2. Discussion of Related Art

Percutaneous transluminal coronary angioplasty (PTCA), stenting and atherectomy are therapeutic medical procedures used to increase blood flow through the coronary arteries. These procedures can often be performed as alternatives to coronary bypass surgery. Percutaneous transluminal angioplasty (PTA) and stenting can often be performed as alternatives to carotid endarterectomy, and femoral-popliteal bypass procedures. In PTCA or PTA procedures, the angioplasty balloon is inflated within the stenosed vessel, at the location of an occlusion, in order to shear and disrupt the wall components of the vessel to obtain an enlarged lumen. In stenting, an endoluminal prosthesis is implanted in the vessel to maintain patency following the procedure. In atherectomy, a rotating blade is used to shear plaque from the arterial wall.

One of the complications associated with all these techniques is the accidental dislodgment of plaque, thrombus or other embolic particulates generated during manipulation of the vessel, thereby causing occlusion of the narrower vessels downstream and ischemia or infarct of the organ which the vessel supplies. Such emboli may be extremely dangerous to the patient, and may result in myocardial infarction, stroke or limb ischemia. In 1995, Waksman et al. disclosed that distal embolization is common after directional atherectomy in coronary arteries and saphenous vein grafts. See Waksman et al., American Heart Journal 129(3): 430–5 (1995). This study found that distal embolization occurs in 28% (31 out of 111) of the patients undergoing atherectomy. In January 1999, Jordan, Jr. et al. disclosed that treatment of carotid stenosis using percutaneous angioplasty with stenting procedure is associated with more than eight times the rate of microemboli seen using carotid endarterectomy. See Jordan, Jr. et al. Cardiovascular Surgery 7(1): 33–8 (1999). Microemboli, as detected by transcranial Doppler monitoring in this study, have been shown to be a potential cause of stroke. The embolic materials include calcium, intimal debris, atheromatous plaque, and thrombi.

In order to initiate these PTCA or PTA procedures, one must first introduce a guidewire into the lumen of the vessel to serve as a conduit for other interventional devices, such as angioplasty balloons and stent delivery systems. This guidewire must be advanced into a position past the location of the occlusion. Guidewires must be capable of traversing tortuous pathways within the body, consisting of bends, loops and branches. For this reason, guidewires need to be flexible, but they should also be sufficiently stiff to serve as conduits for other devices. In addition, they must be "torqueable" to facilitate directional changes as they are guided into position. Guidewires are well known in the art, and are typically made of stainless steel, tantalum or other suitable materials, in a variety of different designs. For example, U.S. Pat. Nos. 4,545,390 and 4,619,274 disclose guidewires in which the distal segment is tapered for greater flexibility. The tapered section may be enclosed in a wire coil, typically a platinum coil, which provides increased column strength and torqueability. Another design is identified in U.S. Pat. No. 5,095,915, where the distal segment is encased in a polymer sleeve with axially spaced grooves to provide bending flexibility.

Vascular filters are also well known in the art, especially vena cava filters, as illustrated in U.S. Pat. Nos. 4,727,873 and 4,688,553. There is also a substantial amount of medical literature describing various designs of vascular filters and reporting the results of clinical and experimental use thereof. See, for example, the article by Eichelter and Schenk, entitled "Prophylaxis of Pulmonary Embolism," Archives of Surgery, Vol. 97 (August, 1968). See, also, the article by Greenfield, et al, entitled "A New Intracaval Filter Permitting Continued Flow and Resolution of Emboli", Surgery, Vol. 73, No. 4 (1973).

Vascular filters are often used during a postoperative period, when there is a perceived risk of a patient encountering pulmonary embolism resulting from clots generated peri-operatively. Pulmonary embolism is a serious and potentially fatal condition that occurs when these clots travel to the lungs. The filter is therefore typically placed in the vena cava to catch and trap clots before they can reach the lungs.

Many of the vascular filters in the prior art are intended to be permanently placed in the venous system of the patient, so that even after the need for the filter has passed, the filter remains in place for the life of the patient. U.S. Pat. No. 3,952,747 describes a stainless steel filtering device that is permanently implanted transvenously within the inferior vena cava. This device is intended to treat recurrent pulmonary embolism. Permanent implantation is often deemed medically undesirable, but it is done because filters are implanted in patients in response to potentially life-threatening situations.

To avoid permanent implantation, it is highly desirable to provide an apparatus and method for preventing embolization associated with angioplasty, stenting or other procedures. In particular, it is desirable to provide a device which can be temporarily placed within the vascular system to collect and retrieve plaque, thrombus and other embolic particulates which have been dislodged during angioplasty, stenting or other procedures. Such a device is removed at the end of the procedure. U.S. Pat. Nos. 5,814,064 and 5,827,324 describe guidewire-based filter devices, wherein the filter is expanded to a predetermined diameter through the introduction of a fluid or a gas. U.S. Pat. No. 5,910,154 describes a guidewire-based filter, which expands to a predetermined diameter through the use of a spring-based actuator. U.S. Pat. No. 6,053,932 describes a guidewire-based filter which expands to a predetermined diameter through the use of a cinch assembly. U.S. Pat. Nos. 6,179,861 and 6,001,118 describe guidewire-based filters where the filter resembles a windsock and is supported by one or more articulated support hoops.

One concern commonly encountered with all these devices is that embolic particulates, once captured, might inadvertently be released during withdrawal of the filter, resulting in emboli which may lodge elsewhere in the vascular system. Another concern commonly encountered with all these devices is that the filter can become full to the point of blocking distal flow, and must then be collapsed, removed and replaced in order to continue the procedure. This complicates the procedure, and also temporarily leaves the site without a filter.

The prior art makes reference to the use of aspiration catheters to remove embolic particulates released during therapeutic procedures. U.S. Pat. No. 6,159,195 describes an occlusion system wherein it is suggested to deploy a separate aspiration catheter to suction embolic material captured in the working space created by the occlusive device positioned in the vessel. U.S. Pat. No. 6,152,909 describes a dual lumen aspiration catheter to be used in therapeutic procedures in conjunction with an occlusive device.

However, the prior art has yet to disclose any guidewire-based vascular filters incorporating means to retrieve embolic particulates from the filters, which can be used to address the clinical problem of avoiding accidental release of embolic particulates, once captured, during angioplasty, stenting or other procedures, and can also be used to address the clinical problem of emptying full guidewire-based filters of embolic particulates which may block distal flow, without the need to collapse, remove and replace the filter in order to continue the angioplasty, stenting or other procedure.

SUMMARY OF THE INVENTION

The present invention provides for a emboli extraction catheter and vascular filter system which can be used to aspirate embolic particulates, so as to avoid their accidental release after they are captured in a guidewire-based vascular filter, and can also be used to empty full guidewire-based vascular filters of embolic particulates which may block distal flow. This invention overcomes many of the concerns associated with the prior art devices, as briefly described above.

In accordance with one aspect, the present invention is directed to an emboli extraction catheter and vascular filter system for insertion into a lumen of a vessel, comprising a guidewire, a basket-shaped vascular filter attached near the distal end of the guidewire, and an emboli extraction catheter. The vascular filter has a smaller first diameter for insertion into the lumen, and a second larger diameter for expanding to substantially equal the diameter of the lumen and to be placed in generally sealing relationship with the lumen. The emboli extraction catheter is a flexible catheter having a radio-opaque tip near the distal end of the catheter, and a hub attached to the proximal end of the catheter. The hub further comprises a sideport and means for maintaining a seal on the guidewire, the lumen of the hub being in fluid communication with the lumen of the catheter.

The vascular filter is inserted into the lumen of a vessel and is used to capture embolic particulates released during interventional procedures. Then, the emboli extraction catheter is inserted over the guidewire, and is positioned as close as possible to the proximal end of the filter. The catheter is then used to aspirate embolic particulates from the filter, so as to avoid their accidental release. It can also be used to empty full vascular filters of embolic particulates which may block distal flow.

In accordance with another aspect, the present invention is directed to an emboli extraction catheter and vascular filter system for insertion into a lumen of a vessel, comprising a guidewire, a basket-shaped vascular filter attached near the distal end of the guidewire, and an emboli extraction catheter. The vascular filter has a smaller first diameter for insertion into the lumen, and a second larger diameter for expanding to substantially equal the diameter of the lumen and to be placed in generally sealing relationship with the lumen. The emboli extraction catheter is a flexible catheter having a radio-opaque tip near the distal end of the catheter, a fluted or serrated shape, or a plurality of longitudinal slits at the distal end of the catheter, and a hub attached to the proximal end of the catheter. The hub further comprises a sideport and means for maintaining a seal on the guidewire, the lumen of the hub being in fluid communication with the lumen of the catheter.

The vascular filter is inserted into the lumen of a vessel and is used to capture embolic particulates released during interventional procedures. Then, the emboli extraction catheter is inserted over the guidewire, and the fluted or serrated shape or longitudinal slits at the distal end of the catheter allow it to be positioned as close as possible to the proximal end of the filter. The catheter is then used to aspirate embolic particulates from the filter, so as to avoid their accidental release. It can also be used to empty full vascular filters of embolic particulates which may block distal flow.

In accordance with another aspect, the present invention is directed to an emboli extraction catheter and vascular filter system for insertion into a lumen of a vessel, comprising a guidewire, a windsock-shaped filter attached near the distal end of the guidewire, and a emboli extraction catheter. The vascular filter has a smaller first diameter for insertion into the lumen, and a second larger diameter for expanding to substantially equal the diameter of the lumen and to be placed in generally sealing relationship with the lumen. The emboli extraction catheter is a flexible catheter having a perforation in the distal portion, with the portion of the catheter distal to the perforation positioned substantially parallel to but offset from the longitudinal axis of the catheter. The emboli extraction catheter further comprises a radio-opaque tip near the distal end of the catheter, and a hub attached to the proximal end of the catheter. The hub further comprises a sideport and means for maintaining a seal on the guidewire, the lumen of the hub being in fluid communication with the lumen of the catheter.

The vascular filter is inserted into the lumen of a vessel and is used to capture embolic particulates released during interventional procedures. Then, the emboli extraction catheter is inserted over the guidewire and into the filter. The catheter is then used to aspirate embolic particulates from the filter, so as to avoid their accidental release. It can also be used to empty full vascular filters of embolic particulates which may block distal flow.

The advantage of the present invention is that the embolic particulates can safely be removed from a vascular filter after they are captured, thereby avoiding their accidental release, which can result in occlusion of the narrower vessels downstream and ischemia or infarct of the organ which the vessel supplies. Another advantage of the present invention is that full filters can be emptied, and distal flow can be restored, without removing and replacing the guidewire-based filter, and without leaving the site temporarily without a filter during the procedure.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE PREFERRED EMBODIMENTS

The emboli extraction catheter and vascular filter system of the present invention is designed to address the clinical problem of avoiding accidental release of embolic particulates after they are captured in a guidewire-based vascular filter, and is also designed to address the clinical problem of emptying full guidewire-based vascular filters of embolic particulates which may block distal flow.

The emboli extraction catheter and vascular filter system comprises a guidewire, a vascular filter attached near the distal end of the guidewire, and an emboli extraction catheter. The vascular filter has a porous covering, a smaller first diameter for insertion into the lumen, and a second larger diameter for expanding to substantially equal the diameter of the lumen and to be placed in generally sealing relationship with the lumen of the vessel. The system comprises actuating means for causing the vascular filter to move from the smaller first diameter to the larger second diameter and back. The emboli extraction catheter is a flexible catheter having an inner lumen, with the guidewire slidably insertable into the lumen. The catheter further comprises a radio-opaque tip near the distal end of the catheter, and a hub, with an inner lumen, attached to the proximal end of the catheter. The hub further comprises a sideport and means for maintaining a seal on the guidewire, with the lumen of the hub being in fluid communication with the lumen of the catheter.

The vascular filter is inserted into the lumen of a vessel and is used to capture embolic particulates released during interventional procedures. Then, the emboli extraction catheter is inserted over the guidewire and is positioned as close as possible to, or into the filter. The catheter is then used to aspirate embolic particulates from the filter, so as to avoid their accidental release. It can also be used to empty full vascular filters of embolic particulates which may block distal flow.

Figure 1:
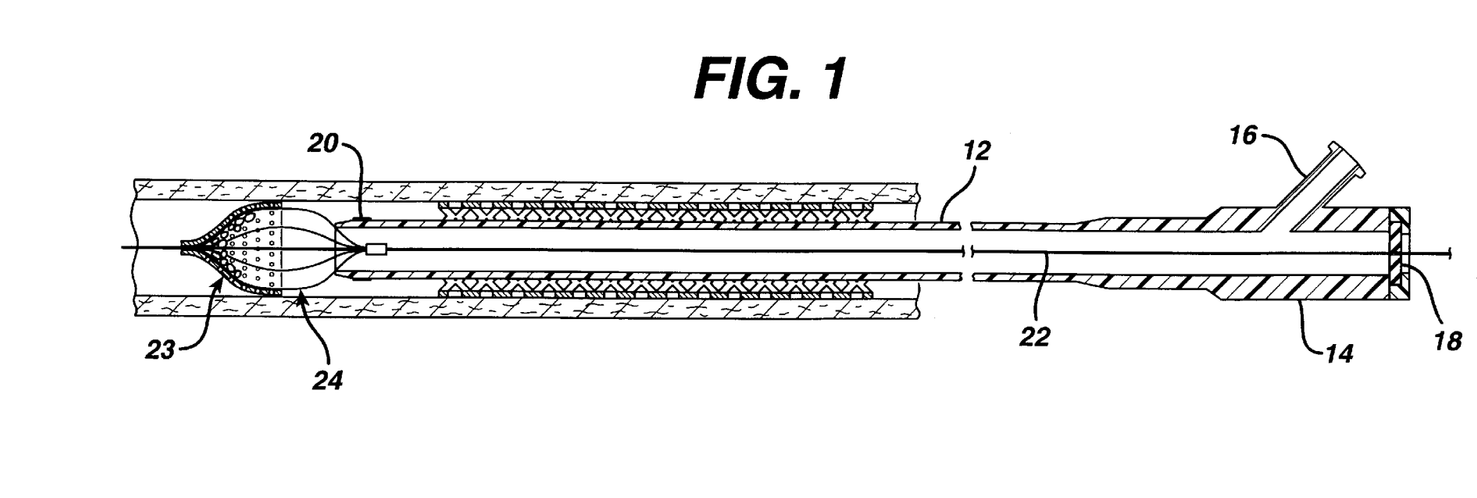
FIG. 1 is a simplified, cross-sectional view of an exemplary embodiment of the emboli extraction catheter and vascular filter system, with the emboli extraction catheter positioned as close as possible to a basket-shaped filter before the aspiration step.

While the present invention may be realized in a number of exemplary embodiments, for ease of explanation, two exemplary embodiments will be described in detail. Referring to the figures wherein like numerals indicate the same element throughout the views, there is shown in FIG. 1, an emboli extraction catheter and vascular filter system made in accordance with the present invention. The vascular filter comprises a guidewire 22 and a basket-shaped filter 24, with a porous covering 23. The emboli extraction catheter comprises a catheter 12, with a radio-opaque tip 20 near the distal end of the catheter 12, and a hub 14 attached to the proximal end of the catheter 12, the hub comprising a sideport 16, and means for maintaining a seal on the guidewire 18. As illustrated in FIG. 1, the lumen of the catheter 12 is in fluid communication with the lumen of the hub 14. Therefore, as illustrated in FIG. 1, the distal end of the catheter 12 has been slidably inserted over the proximal end of the guidewire 22. As illustrated in FIG. 1, the guidewire 22 is now coaxially disposed within the catheter 12, and the radio-opaque tip 20 on the catheter 12 allows the operator to visualize when the distal end of the catheter 12 is as close as possible to the proximal end of the basket-shaped filter 24.

Figure 2:
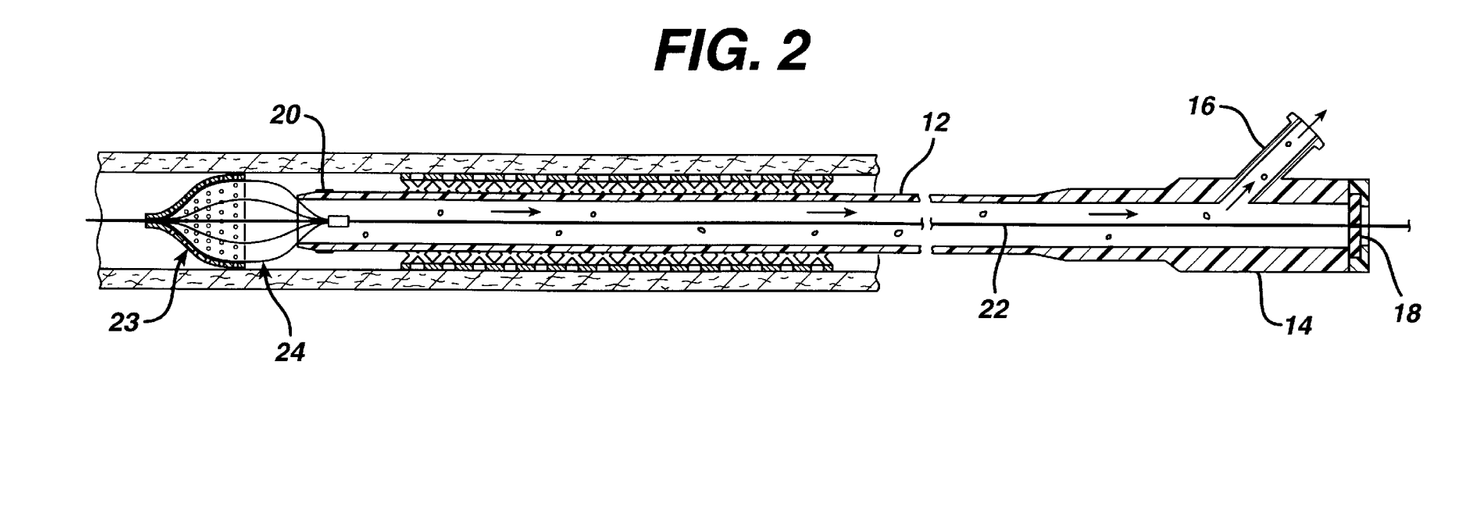
FIG. 2 is a simplified, cross sectional view of an exemplary embodiment of the emboli extraction catheter and vascular filter system, with the emboli extraction catheter positioned as close as possible to a basket-shaped filter during the aspiration step.

FIG. 2 shows an exemplary embodiment of the emboli extraction catheter and vascular filter system made in accordance with the present invention. As illustrated in FIG. 2, when the radio-opaque tip 20 is positioned as close as possible to the basket-shaped filter 24, a syringe may be attached to the sideport 16 to aspirate the column of blood and embolic particulates from the filter 24.

Figure 3A:
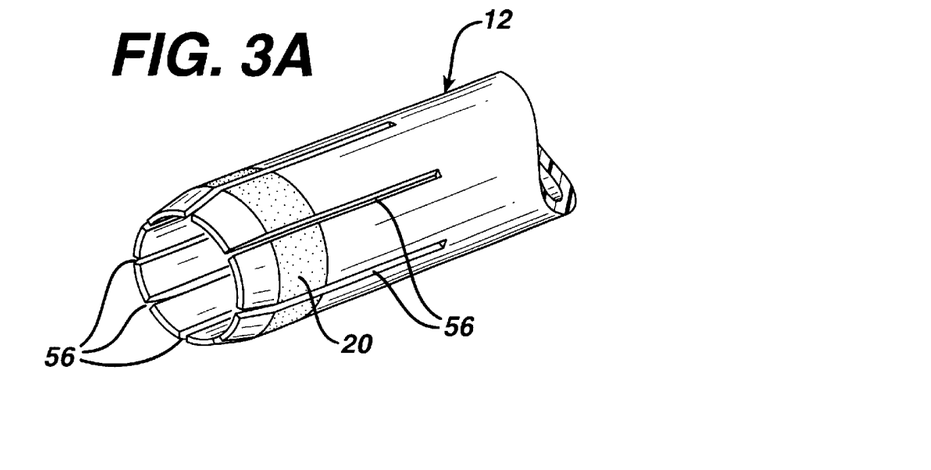
FIGS. 3A, 3B and 3C are simplified, enlarged, partial cross-sectional views of other exemplary embodiments of the emboli extraction catheter and vascular filter system, wherein the distal tip of the emboli extraction catheter is fluted, serrated or slit.
Figure 3B:
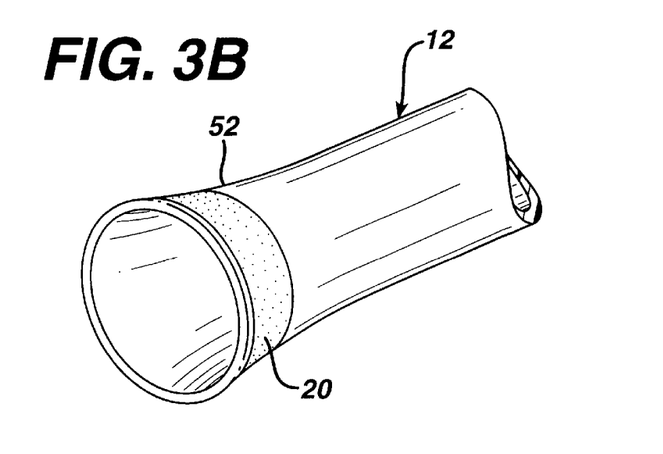
Figure 3C:
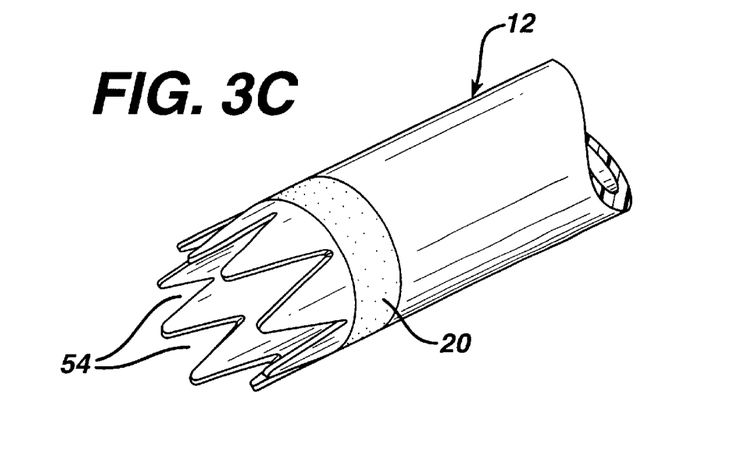

FIGS. 3A, 3B and 3C shows partial views of the distal end of an emboli extraction catheter made in accordance with the present invention. As illustrated in FIG. 3A, the distal end of the catheter may comprise a plurality of slits 56, to allow the emboli extraction catheter 12 to be positioned as close as possible to the basket-shaped filter 24, so as to avoid accidental release of embolic particulates during the aspiration step. As illustrated in FIG. 3B, the distal end of the catheter may be fluted 52, to allow the emboli extraction catheter 12 to be positioned as close as possible to the basket-shaped filter 24, so as to avoid accidental release of embolic particulates during the aspiration step. As illustrated in FIG. 3C, the distal end of the catheter may be serrated 54, to allow the emboli extraction catheter 12 to be positioned as close as possible to the basket-shaped filter 24, so as to avoid accidental release of embolic particulates during the aspiration step.

The basket-shaped vascular filter 24 and the guidewire 22 may be made from any number of suitable materials, and are preferably made from a superelastic alloy such as Nickel-Titanium. The porous covering 23 on the basket-shaped filter 24 may be made from any number of suitable materials, and is preferably made from a flexible polymeric material with elastomeric properties chosen from a group consisting of polyurethane, polyethylene or a co-polymer thereof. The porous covering 23 on the filter 24 may comprise any number and configuration of pores and preferably comprises regularly-spacer laser-formed holes wherein the pore size is from about 20 to about 300 microns. The filter may be deployed by any suitable means, and is preferably deployed through the use of a sheath, which covers and restrains the filter during insertion into the lumen, is retracted thereafter to allow the filter to achieve its maximum diameter, then is advanced over the filter to cover and restrain it during removal of the guidewire and filter. The emboli extraction catheter 12 may be made from any number of suitable materials, and is preferably made from commercially available polymers, such as polyamide, high or low-density polyethylene, polyimide or polyurethane. The distal shaft of the emboli extraction catheter 12 may be constructed from any number of suitable materials, and is preferably constructed from lower durometer material than the proximal shaft of the emboli extraction catheter, to facilitate tracking and to avoid trauma to the artery. The distal shaft of the emboli extraction catheter 12 may also comprise a flexible coil to maintain flexibility and to prevent collapse of the catheter lumen during the aspiration step. The proximal shaft of the emboli extraction catheter 12 may be constructed from any number of suitable materials, and is preferably reinforced with braid wire to enhance pushability.

The exemplary embodiment of the emboli extraction catheter, as illustrated in FIGS. 1, 2 and 3, can be used to aspirate embolic particulates, so as to avoid their accidental release after they are captured in a vascular filter, and can also be used to empty full vascular filters of embolic particulates which may block distal flow.

Once the guidewire 22, comprising a filter 24, has been inserted into a vessel and has been used to collect embolic particulates which have been dislodged during angioplasty, stenting or other procedures, the emboli extraction catheter 12 can then be inserted over the guidewire. When the radio-opaque tip 20 of the catheter 12 is visualized to be as close as possible to the proximal end of the filter 24, the emboli extraction catheter 12 is in position. At this point, a syringe may be attached to the sideport 16 to aspirate the column of blood and embolic particulates from the filter 24. Once the embolic particulates have been aspirated, the syringe may be removed from the sideport 16, and the emboli extraction catheter 10 may be removed from the vessel. If the interventional procedure is complete, the guidewire 22 and filter 24 may also be removed at this point, without concern regarding accidental release of embolic particulates. If the interventional procedure is incomplete, the guidewire 22 and filter 24 may remain in position, and may collect additional embolic particulates, while still permitting distal flow.

Figure 4:
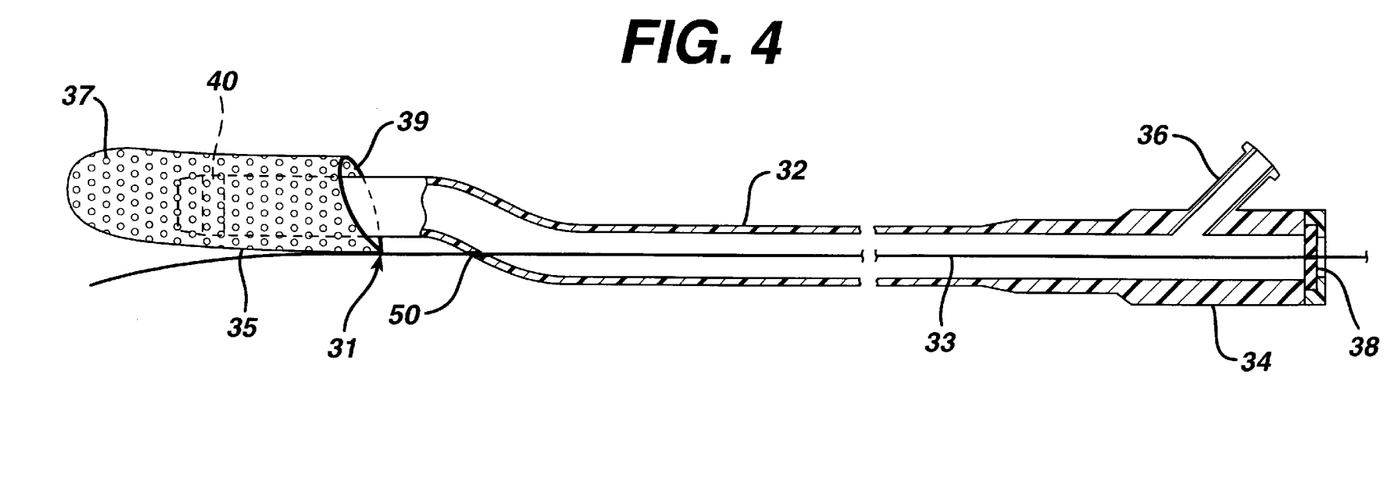
FIG. 4 is a simplified, cross-sectional view of an exemplary embodiment of the emboli extraction catheter and vascular filter system, with the emboli extraction catheter positioned as close as possible to a windsock-shaped filter before the aspiration step.

FIG. 4 shows another exemplary embodiment of the emboli extraction catheter and vascular filter system made in accordance with the present invention. The vascular filter device comprises a guidewire 33 and a windsock-shaped filter 35. The windsock-shaped filter 35 comprises at least one support hoop 39, having an articulation region 31, and a porous flexible sac 37 affixed to the at least one support hoop 39 at the greatest distance from the distal end of the guidewire 33, so that the support hoop 39 forms the mouth of the porous flexible sac 37. The emboli extraction catheter comprises a catheter 32, a radio-opaque tip 40 near the distal end of the catheter 32, and a hub 34 attached to the proximal end of the catheter 32, the hub comprising a sideport 36, and means for maintaining a seal on the guidewire 38. The catheter 32 further comprises a perforation 50 near the distal end of the catheter 32. The portion of the emboli extraction catheter 32 distal to the perforation 50 is positioned substantially parallel to but offset from the longitudinal axis of the catheter 32. As illustrated in FIG. 4, the lumen of the catheter 32 is in fluid communication with the lumen of the hub 34. Therefore, as illustrated in FIG. 4, the proximal end of the guidewire 33 has been slidably inserted into the perforation 50 near the distal end of the catheter. As illustrated in FIG. 4, the guidewire 33 is now coaxially disposed within the portion of the catheter proximal to the perforation 50, and the radio-opaque tip 40 on the catheter 32 allows the operator to visualize when the distal end of the catheter 32 has been inserted through the support hoop 39 and into the porous flexible sac 37 of the windsock-shaped filter 35.

As illustrated in FIG. 4, when the radio-opaque tip 40 has been inserted into the filter 35, then the system is ready for the aspiration step. A syringe may then be attached to the sideport 36 to aspirate the column of blood and embolic particulates from the filter 35.

The at least one support hoop 39 of the windsock-shaped filter 35, and the guidewire 33, may be made from any number of suitable materials, and are preferably made from a superelastic alloy such as Nickel-Titanium. The porous flexible sac 37 on the windsock-shaped filter 35 may be made from any number of suitable materials, and is preferably made from a flexible polymeric material with elastomeric properties chosen from a group consisting of polyurethane, polyethylene or a co-polymer thereof. The porous flexible sac 37 on the windsock-shaped filter 35 may comprise any number and configuration of pores and preferably comprises regularly-spacer laser-formed holes wherein the pore size is from about 20 to about 300 microns.

The filter may be deployed by any suitable means, and is preferably deployed through the use of a sheath, which covers and restrains the filter during insertion into the lumen, is retracted thereafter to allow the filter to achieve its maximum diameter, then is advanced over the filter to cover and restrain it during removal of the guidewire and the filter. The emboli extraction catheter 32 may be made from any number of suitable materials, and is preferably made from commercially available polymers, such as polyamide, high or low density polyethylene, polyimide or polyurethane. The distal shaft of the emboli extraction catheter 32 may be constructed from any number of suitable materials, and is preferably constructed from lower durometer material than the proximal shaft of the emboli extraction catheter, to facilitate tracking and to avoid trauma to the artery. The distal shaft of the emboli extraction catheter 32 may also comprise a flexible coil to maintain flexibility and to prevent collapse of the catheter lumen during the aspiration step. The proximal shaft of the emboli extraction catheter 32 may be constructed from any number of suitable materials, and is preferably reinforced with braid wire to enhance pushability.

The exemplary embodiment of the emboli extraction catheter, as illustrated in FIG. 4, can be used to aspirate embolic particulates, so as to avoid their accidental release after they are captured in a vascular filter, and can also be used to empty full vascular filters of embolic particulates which may block distal flow. Once the guidewire 33, comprising a filter 35, has been inserted into a vessel and has been used to collect embolic particulates which have been dislodged during angioplasty, stenting or other procedures, the emboli extraction catheter 32 can then be inserted over the guidewire 33 by inserting the proximal end of the guidewire 33 into the perforation 50 near the distal end of the catheter 32. When the radio-opaque tip 40 is visualized to have been inserted into the filter 35, the emboli extraction catheter 32 is in position. At this point, a syringe may be attached to the sideport 36 to aspirate the column of blood and embolic particulates from the filter 35. Once the embolic particulates have been aspirated, the syringe may be removed from the sideport 36, and the emboli extraction catheter 32 may be removed from the vessel. If the interventional procedure is complete, the guidewire 33 with filter 35 may also be removed at this point, without concern regarding accidental release of embolic particulates. If the interventional procedure is incomplete, the guidewire 33 with filter 35 may remain in position, and may collect additional embolic particulates, while still permitting distal flow.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to include all modifications that may fall within the scope of the appended claims.

That which is claimed is:

1. An emboli extraction catheter and vascular filter system for insertion into a lumen of a vessel, said system comprising:
   a) a guidewire having a proximal end and a distal end;
   b) a vascular filter attached near said distal end of said guidewire, said filter comprising a proximal portion, a distal portion, and a plurality of struts extending therebetween, said filter further comprising a porous flexible filter membrane, with said porous flexible filter membrane connected to said filter distal portion and said plurality of struts, said porous filter membrane having a length less than the length of said plurality of struts, said vascular filter having a smaller first diameter for insertion into said lumen, and a second larger diameter for expanding to substantially equal the diameter of said lumen and to be placed in generally sealing relationship with said lumen;

c) actuating means for causing said vascular filter to move from said smaller first diameter to said larger second diameter and back to said smaller first diameter;

d) a flexible catheter having an outer diameter and an inner diameter, a proximal end and a distal end, a proximal portion and a distal portion, and an inner lumen, with said proximal end of said guidewire slidably insertable into said distal end of said catheter wherein said distal end of said catheter comprises a plurality of longitudinal slits;

e) a radio-opaque tip near said distal end of said catheter; and f) a hub permanently attached to said proximal end of said catheter, said hub having an outer diameter and an inner diameter, a proximal end and a distal end, and an inner lumen, said hub further comprising a sideport and means for maintaining a seal on the guidewire, said lumen of said hub being in fluid communication with said lumen of said catheter; wherein said vascular filter and said catheter slits engage one another upon retraction of said filter into said catheter during aspiration of said catheter.

2. The emboli extraction catheter and vascular filter system according to claim 1, wherein said guidewire is made from Nickel-Titanium alloy.

3. The emboli extraction catheter and vascular filter system according to claim 1, wherein said vascular filter is made from Nickel-Titanium alloy.

4. The emboli extraction catheter and vascular filter system according to claim 1, wherein said porous flexible filter membrane is made from a flexible polymeric material chosen from a group consisting of polyurethane, polyethylene or a co-polymer thereof.

5. The emboli extraction catheter and vascular filter system according to claim 1, wherein the pore size of said porous flexible filter membrane is from about 20 to about 300 microns.

6. The emboli extraction catheter and vascular filter system according to claim 1, wherein said actuating means is a sheath.

7. The emboli extraction catheter and vascular filter system according to claim 1, wherein said catheter is made from a polymeric material.

8. The emboli extraction catheter and vascular filter system according to claim 1, wherein said proximal portion of said catheter is reinforced with braid wire.

9. The emboli extraction catheter and vascular filter system according to claim 1, wherein said proximal portion of said catheter comprises a flexible coil.

10. The emboli extraction catheter and vascular filter system according to claim 1, wherein said distal portion of said catheter is constructed of lower durometer material than said proximal portion of said catheter.

11. A method for capturing embolic particulates within a vascular filter in the lumen of a vessel, and retrieving them at the end of the procedure, comprising the steps of:

a) inserting a guidewire into said lumen, said guidewire having a proximal end and a distal end, and a vascular filter attached near said distal end of said guidewire, said filter comprising a proximal portion, a distal portion, and a plurality of struts extending therebetween, said filter further comprising a porous flexible filter membrane, said vascular filter having a smaller first diameter for insertion into said lumen, and a second larger diameter for expanding to substantially equal the diameter of said lumen and to be placed in generally sealing relationship with said lumen;

b) advancing said guidewire until said distal end of said guidewire is positioned past a vascular occlusion in said vessel;

c) deploying said filter in said lumen, distal to said vascular occlusion;

d) advancing additional interventional devices over said guidewire, and positioning said devices at the site of said occlusion in said vessel;

e) performing additional procedures to therapeutically treat said occlusion in said vessel;

f) capturing embolic particulates generated by said procedures in said filter;

g) removing said interventional devices from said guidewire;

h) slidably inserting a flexible catheter over said guidewire, said flexible catheter comprising an outer diameter and an inner diameter, a proximal end and a distal end, and an inner lumen, a radio-opaque tip near said distal end of said catheter, and a hub permanently attached to said proximal end of said catheter, said hub having an outer diameter and an inner diameter, a proximal end and a distal end, and an inner lumen, said lumen of said hub being in fluid communication with said lumen of said catheter, said hub further comprising a sideport and means for maintaining a seal on said guidewire;

i) advancing said flexible catheter over said guidewire until said radio-opaque tip engages said proximal portion of said filter;

j) attaching a syringe to said sideport of said hub;

k) using said syringe to aspirate said embolic particulates from said filter;

l) removing said catheter from said lumen;

m) collapsing said filter in said lumen; and n) removing said guidewire and said filter from said lumen.

12. A method for capturing embolic particulates within a vascular filter in the lumen of a vessel, and retrieving them during the procedure, comprising the steps of:

a) inserting a guidewire into said lumen, said guidewire having a proximal end and a distal end, and a vascular filter attached near said distal end of said guidewire, said filter comprising a proximal portion, a distal portion, and a plurality of struts extending therebetween, said filter further comprising a porous flexible filter membrane, said vascular filter having a smaller first diameter for insertion into said lumen, and a second larger diameter for expanding to substantially equal the diameter of said lumen and to be placed in generally sealing relationship with said lumen;

b) advancing said guidewire until said distal end of said guidewire is positioned past a vascular occlusion in said vessel;

c) deploying said filter in said lumen, distal to said vascular occlusion;

d) advancing additional interventional devices over said guidewire, and positioning said devices at the site of said occlusion in said vessel;

e) performing additional procedures to therapeutically treat said occlusion in said vessel;

f) capturing embolic particulates generated by said procedures in said filter;

g) removing said interventional devices from said guidewire;

h) slidably inserting a flexible catheter over said guidewire, said flexible catheter comprising an outer diameter and an inner diameter, a proximal end and a distal end, and an inner lumen, a radio-opaque tip near said distal end of said catheter; and a hub permanently attached to said proximal end of said catheter, said hub having an outer diameter and an inner diameter, a proximal end and a distal end, and an inner lumen, said lumen of said hub being in fluid communication with said lumen of said catheter, said hub further comprising a sideport and means for maintaining a seal on said guidewire;

i) advancing said flexible catheter over said guidewire until said radio-opaque tip engages said proximal portion of said filter;

j) attaching a syringe to said sideport of said hub;

k) using said syringe to aspirate said embolic particulates from said filter;

l) removing said catheter from said lumen; and m) advancing additional interventional devices over said guidewire to complete therapeutic treatment of said occlusion in said vessel.

* * * * *